United States Patent [19]

Oestreicher et al.

[11] 4,118,217

[45] Oct. 3, 1978

[54] HERBICIDALLY ACTIVE SUBSTITUTED PYRIMIDINE COMPOUNDS AND METHOD OF USING SAME

[75] Inventors: Stephen L. Oestreicher, Mission, Kans.; David P. Hardin, North Kansas City, Mo.

[73] Assignee: Farmland Industries, Incorporated, Kansas City, Mo.

[21] Appl. No.: 757,481

[22] Filed: Jan. 6, 1977

[51] Int. Cl.$^2$ ............................................. A01N 9/22
[52] U.S. Cl. .......................................... 71/92; 71/76;
544/318; 544/319; 544/329; 544/334
[58] Field of Search .................. 71/92, 76; 424/251 R

[56] References Cited

U.S. PATENT DOCUMENTS

| | | | |
|---|---|---|---|
| 3,126,271 | 3/1964 | Thomson et al. | 71/92 |
| 3,317,542 | 5/1967 | Haszeldine et al. | 71/94 |
| 3,317,549 | 5/1967 | Johnston | 71/94 |
| 3,637,716 | 1/1972 | Bimber et al. | 71/94 |
| 3,836,352 | 9/1974 | Phillips | 71/94 |
| 3,845,055 | 10/1974 | Hoegerle et al. | 71/92 |
| 3,948,914 | 4/1976 | Fischer | 71/92 |

FOREIGN PATENT DOCUMENTS 220,776   6/1956   Australia ...................... 71/92

*Primary Examiner*—Glennon H. Hollrah

*Attorney, Agent, or Firm*—Schmidt, Johnson, Hovey & Williams

[57] ABSTRACT

Substituted pyrimidine compounds particularly useful as selective post-emergent herbicides are described for inhibiting the growth of and killing undesirable plants and weeds. The compounds hereof include 2,4-substituted pyrimidine-5-carboxylates having the general formula

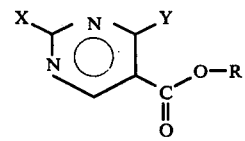

wherein X, Y and R represent specific types and classes of substituent groups. Especially preferred compounds in accordance with the invention include octyl 2,4-dichloropyrimidine-5-carboxylate, benzyl 2,4-dichloropyrimidine-5-carboxylate, allyl 2,4-dichloropyrimidine-5-carboxylate, ethyl 4-chloro-2-mercaptopyrimidine-5-carboxylate, butyl 2-chloro-4-di-n-propylaminopyrimidine-5-carboxylate. The compounds may be applied by conventional spray techniques at a dosage rate of from about ¼ to 20 pounds per acre to good effect.

9 Claims, No Drawings

HERBICIDALLY ACTIVE SUBSTITUTED PYRIMIDINE COMPOUNDS AND METHOD OF USING SAME

This invention relates to a method for the post emergent control of undesirable plants such as weeds through the application of specific 2,4-substituted pyrimidine-5-carboxylates.

Considerable search effort has been expended in the past in the preparation and testing of various compounds for use as herbicides. A number of these investigations have developed highly useful herbicidal agents such as phenoxy and triazine compounds. A prime goal in developing such herbicides is that of selectivity, i.e., a herbicide that will operate only under specific conditions such as pre-emergent or post-emergent, or one that will kill only undesirable weeds without substantially harming a growing crop. Of course, no one compound or class thereof has been developed to provide absolute selectivity, but considerable advances have been made in this area.

In many cases it is desirable to have a class of herbicides which have good post-emergent activity, but little if any pre-emergent activity. This obviates the problem of carryover experienced with pre-emergent herbicides wherein the activity of the applied compounds carries over into the next growing season with adverse effects on the desired crop. Furthermore, effective post-emergent herbicides do not have to be applied at critical times as is the case with some pre-emergent herbicides.

It is therefore the most important object of the present invention to provide a series of relatively selective herbicides having excellent post-emergent properties but with little if any pre-emergent activity, so that the herbicides can be applied to post-emergent plants without fear of carryover problems into the next growing season.

As a corollary to the foregoing, another object of the invention is to provide post-emergent herbicides in the group of 2,4-substituted pyrimidine-5-carboxylates which can be applied by spraying or other means onto plants for controlling weeds.

In accordance with the invention, it has been determined that certain 2,4-substituted pyrimidine-5-carboxylates can be applied in herbicidally effective amounts as post-emergent herbicides for inhibiting the growth of and/or killing undesirable weeds. The compounds are selected from the group consisting of (A) compounds of the formula

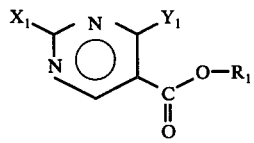

wherein $X_1$ represents a halogen, $Y_1$ is selected from the group consisting of the halogens, alkylamino groups having from 1 to 6 carbon atoms, inclusive, hydroxyalkylamino groups having from 2 to 6 carbon atoms, inclusive, and alkoxy groups having from 1 to 6 carbon atoms, inclusive, and $R_1$ is selected from the group consisting of alkyl groups having from 1 to 18 carbon atoms, inclusive, benzyl groups, chlorophenyl groups, chlorobenzyl groups, trichloromethylalkyl groups having from 1 to 6 carbon atoms, inclusive, alkylphenyl groups having from 1 to 6 carbon atoms, inclusive, and alkenyl groups having from 3 to 6 carbon atoms, inclusive, and (B) compounds of the formula

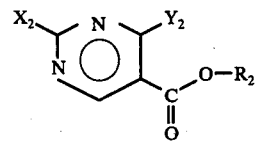

wherein $X_2$ is selected from the group consisting of the halogens, alkoxy groups having from 1 to 6 carbon atoms, inclusive, alkylthio groups having from 1 to 6 carbon atoms, inclusive, and mercapto groups, $Y_2$ represents a halogen, and $R_2$ is selected from the group consisting of alkyl groups having from 1 to 18 carbon atoms, inclusive, benzyl groups, chlorophenyl groups, chlorobenzyl groups, trichloromethylalkyl groups having from 1 to 6 carbon atoms, inclusive, alkylphenyl groups having from 1 to 6 carbon atoms, inclusive, and alkenyl groups having from 3 to 6 carbon atoms, inclusive.

The term alkyl as used herein is in all instances intended to encompass these cycloalkyl and dialkyl compounds within the group definitions hereof.

Particularly preferred compounds in accordance with the above definition include octyl 2,4-dichloropyrimidine-5-carboxylate, benzyl 2,4-dichloropyrimidine-5-carboxylate, allyl 2,4-dichloropyrimidine-5-carboxylate, ethyl 4-chloro-2-mercaptopyrimidine-5-carboxylate, and butyl 2-chloro-4-di-n-propylaminoyrimidine-5-carboxylate.

In order to outline certain other herbicidally active compounds produced in accordance with the invention, the following table is presented. The numbers assigned each of the respective compounds are used hereinafter in connection with additional examples and test results.

TABLE I

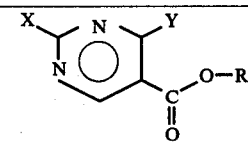

| No. | X | Y | R |
|---|---|---|---|
| 577 | —Cl | —Cl | —(CH$_2$)$_3$CH$_3$ |
| 584 | —Cl | —NHCH(CH$_3$)$_2$ | —(CH$_2$)$_3$CH$_3$ |
| 585 | —Cl | —OCH$_3$ | —(CH$_2$)$_3$CH$_3$ |
| 586 | —OCH$_3$ | —Cl | —(CH$_2$)$_3$CH$_3$ |
| 590 | —Cl | —Cl | —(CH$_2$)$_3$CH$_3$ |
| 593 | —Cl | —N(CH$_2$CH$_2$CH$_3$)$_2$ | —(CH$_2$)$_3$CH$_3$ |
| 599 | —SCH$_3$ | —Cl | —C$_2$H$_5$ |
| 600 | —Cl | —NHCH$_2$CHOHCH$_3$ | —(CH$_2$)$_3$CH$_3$ |
| 603 | —OCH$_3$ | —Cl | —C$_2$H$_5$ |
| 605 | —SH | —Cl | —C$_2$H$_5$ |
| 608 | —Cl | —Cl | —C$_2$H$_5$ |
| 610 | —Cl | —Cl | —CH$_2$CCl$_3$ |
| 612 | —Cl | —NHCH(CH$_3$)$_2$ | —CH$_2$CCl$_3$ |
| 613 | —Cl | —NH—◁ | —(CH$_2$)$_3$CH$_3$ |
| 617 | —Cl | —Cl | —CH$_2$C$_6$H$_5$ |
| 619 | —Cl | —Cl | —CH$_3$ |
| 625 | —Cl | —Cl | —CH$_2$-C$_6$H$_3$Cl$_2$ |
| 633 | —Cl | —Cl | C$_6$H$_3$Cl$_2$ |
| 634 | —Br | —Br | —(CH$_2$)$_3$CH$_3$ |
| 640 | —Cl | —Cl | —CH$_2$CH=CH$_2$ |
| 647 | —Cl | —Cl | —(CH$_2$)$_{17}$CH$_3$ |

TABLE I-continued

[Structure: pyrimidine ring with X, Y substituents and C(=O)O—R group]

| No. | X | Y | R |
|-----|-----|-----|-----|
| 648 | —Cl | —Cl | —CH(CH₃)₂ |
| 650 | —Cl | —Cl | —⟨phenyl⟩—C₂H₅ |

Essentially all of the compounds of the invention are insoluble in water, but are soluble in common organic solvents such as acetone or ethanol. This is advantageous for post-emergent applications, since it is necessary that the herbicides penetrate the waxy integument covering the surfaces of weeds. Thus, in a lipophilic phase such as occurs when the compounds are dispersed in organic solvent, the compounds hereof are believed to penetrate the integument and are therefore highly advantageous for post-emergent application.

In the latter connection, the preferred method of application involves dispersing a herbicidally effective amount of a compound of the invention (or mixtures thereof) in a solvent and spraying the resultant dispersion over an area where the post-emergent plants are growing. In most cases the compounds hereof are advantageously applied at a dosage rate of from about ¼ to 20 pounds per acre, and most preferably at a rate of from about ½ to 10 pounds per acre, depending on variables such as stage of weed development, type of formulation, weed species and weather conditions. Of course, the particular amount to be used may vary in certain circumstances, depending upon the type and extent of the weeds to be killed. In addition, the compounds hereof may also be applied in the forms of powders or dusts by mixing with inert carriers or diluents such as talc, diatomaceous earth or clays. Aerosols containing the compounds of the invention can also be prepared for small applications.

A further advantage of the herbicides hereof stems from the fact that they can be prepared in good yield using essentially conventional techniques. For example, octyl 2,4-dichloropyrimidine-5-carboxylate (No. 590) was synthesized by mixing uracil-5-carboxylic acid (4.35 g.), thionylchloride (25 ml.), and pyridine (0.125 ml.) and stirring at room temperature for five hours, followed by refluxing for sixteen hours. After cooling, the solid product was recovered by filtration, washed with n-hexane until the odor of sulfur dioxide was absent, and dried (3.9 g.). This product (uracil-5-carbonylchloride) is an off-white powder which decomposes above about 230° C.

The uracil-5-carbonylchloride was next refluxed in 200 milliliters of n-octanol until the solid was substantially dissolved. The mixture was then cooled and the white precipitate recovered by filtration. The solid was next washed with 100 milliliters of diethyl ether and dried (5.14 g., mp 226°–8° C.).

Four grams of the above ester was next suspended in phosphoryl chloride (40 ml), and N,N-diethylaniline (6 ml) was added slowly. After standing at room temperature for 10 minutes, the mixture was heated gently until a solution occurred, and then refluxed for 2 hours. The volume was then reduced to about one-half by vacuum distillation and the residue poured slowly over 200 g. of ice and water. After stirring for 10 minutes, the water mixture was extracted with 4 aliquots (50 ml) of diethyl ether. The ether solutions were washed with dilute aqueous hydrochloric acid (30 ml), saturated sodium bicarbonate solution (30 ml), water (60 ml), and saturated brine (30 ml); dried over magnesium sulfate (anhydrous) and the solvent removed. The oily residue was dissolved in hexane and treated with decolorizing charcoal, and solvent removed. The residue was vacuum distilled. 1.59 grams of compound No. 590 was obtained.

Compounds Nos. 617 and 640 were produced in a method identical to that described above save for the use of the appropriate alcohol in each case, i.e., benzyl alcohol and allyl alcohol.

Ethyl-4-chloro-2-mercaptopyrimidine-5-carboxylate (No. 605) was produced by the following method. Ethyl 2-thiouracil-5-carboxylate (1.0g) was refluxed 20 hours after solution in phosphoryl chloride (30 ml). The volume was reduced by ½ by vacuum distillation and the residue poured onto 150 g ice/water. After stirring a few minutes, the water mixture was extracted with 3 × 100 ml dichloromethane. The dichloromethane extract was washed with water (50 ml), dilute aq. sodium bicarbonate (50 ml), water (50 ml), dried over magnesium sulfate (anhydrous), and the solvent removed. The residue was extracted with boiling ethanol and the extract treated with decolorizing charcoal, and the solvent removed. This residue was dissolved in dichloromethane, dried over magnesium sulfate (anhydrous) and solvent removed leaving 0.36 g of compound No. 605, a low melting solid.

Butyl 2-chloro-4-di-n-propylaminopyrimidine-5-carboxylate (No. 593) was produced in accordance with the following method. Di-n-propylamine was added at room temperature with stirring to water (20 ml) over dichloromethane (20 ml) containing 1.0 g butyl-2,4-dichloropyrimidine-5-carboxylate (prepared similarly as in synthesis of No. 590) with gas chromatographic monitoring. When the pyrimidine has been completely consumed, addition of the amine was stopped. The phases were separated, and the dichloromethane phase washed with water (3 × 20 ml), dried over magnesium sulfate (anhydrous), and the solvent removed. The residue was dissolved in n-hexane, treated with decolorizing charcoal; charcoal and solvent were then removed. 0.95 g of Compound No. 593 was obtained.

In addition to the three methods described above, certain compounds of the invention can be prepared by treating the appropriate pyrimidine ester with an equivalent of the proper sodium alkoxide in dichloromethane at 0° C., followed by suitable recovery methods such as extraction, column chromatography or other methods well known to those skilled in the art.

The following example will illustrate the herbicidal properties of compounds in accordance with the invention, but nothing therein is to be taken as a limitation upon the scope of the invention.

EXAMPLE

Appropriate crop and weed species were seeded in individual 83 or 250 sq. in. trays lined with polyethylene and watered in amounts adequate to moisten the soil. The trays were maintained under greenhouse conditions, and when all weeds and crops reached suitable growth development, generally first leaf stage, those appropriate to pertaining test requirements were selected for uniformity of growth and development. In general, tests were carried out in duplicate for each dosage rate.

The respective test compounds were dissolved in acetone, ethanol or other appropriate solvents and diluted to a spray volume equivalent to 20 gallons per acre. The solutions were applied with a hand held aspirator applicator using a halocarbon propellant in a fume hood, and, after application, the trays were removed to the greenhouse and held for observation.

The following Table II sets forth the results of this series of tests. In each individual test the dosage rate specified was used, and the rating scale ranged from 0 (no effect) to 10 (complete kill). The compounds numbers set forth in Table I have been used in Table II:

scale ranged from 0 (no damage) to 10 (complete kill). This data is given in the following Table III:

TABLE III

| Compound No. | Overall Phyto Rating | Weeds Only | Crops Only | Corn & Milo Only |
|---|---|---|---|---|
| 577 | 6.1 | 8.0 | 4.2 | 4.0 |
| 584 | 4.6 | 6.5 | 2.0 | 2.0 |
| 585/586 | 4.6 | 7.5 | 0.7 | 1.0 |
| 590 | 6.0 | 7.8 | 4.2 | 4.0 |
| 593 | 2.6 | 4.5 | 0.8 | 0.5 |
| 599 | 7.2 | 8.5 | 6.0 | 4.0 |
| 603 | 5.5 | 7.0 | 4.0 | 2.0 |
| 605 | 4.5 | 6.5 | 2.5 | 1.0 |
| 608 | 7.9 | 9.5 | 6.2 | 4.0 |
| 610 | 5.1 | 6.3 | 4.2 | 3.5 |
| 613 | 3.1 | 3.8 | 2.5 | 0 |
| 617 | 3.9 | 5.6 | 1.8 | 0.8 |
| 640 | 6.0 | 7.4 | 4.3 | 3.5 |

TABLE II

| Compound No. | Dosage Rate | Corn | Cotton | Milo | Soybeans | Pigweed | Velvet Leaf | Yellow Foxtail | Barnyard Grass | Dock | Black Medic/ Alfalfa |
|---|---|---|---|---|---|---|---|---|---|---|---|
| 577 | 5 lbs./acre | 3 | — | 5 | — | 10 | 9 | 6 | — | 9 | — |
| 577 | 2 | 3 | — | 3 | — | 10 | 7 | 8 | — | — | 9 |
| 577 | 1 | 2 | — | 2 | — | 7 | 2 | 5 | — | — | 6 |
| 577 | ½ | 1 | — | 1 | — | 5 | 2 | 4 | — | — | 6 |
| 577 | ¼ | 0 | — | 0 | — | 2 | 0 | 4 | — | — | 3 |
| 577 | 5 | 3 | 5 | 5 | 4 | 10 | 9 | 5 | — | — | 8 |
| 584 | 5 | 2 | 2 | 2 | — | 9 | 5 | 5 | — | — | 7 |
| 584 | 5 | 0 | 0 | 2 | 2 | 10 | 3 | 2 | — | — | 4 |
| 584 | 10 | 1 | 2 | 3 | 0 | 9 | 3 | 6 | — | — | 5 |
| [1]585/586 | 5 | 2 | — | 4 | — | 8 | 7 | 5 | — | — | 8 |
| 585/586 | 5 | 0 | — | 2 | 0 | 10 | 3 | 9 | — | — | 8 |
| 585/586 | 10 | 3 | — | 3 | — | 10 | 6 | 8 | — | — | 9 |
| 590 | 2½ | 4 | — | 4 | — | — | 5 | 7 | — | — | 10 |
| 590 | 5 | 3 | 5 | 5 | 4 | 10 | 4 | 8 | — | — | 9 |
| 593 | 2½ | 0 | — | 0 | — | — | 0 | 0 | — | — | 0 |
| 593 | 5 | 1 | 0 | 2 | 0 | 9 | 2 | 2 | — | — | 5 |
| 593 | 10 | 1 | 0 | 0 | 2 | — | 2 | 4 | 2 | 1 | — |
| 599 | 2½ | 0 | — | 0 | — | — | 5 | 3 | — | — | 0 |
| 599 | 5 | 3 | 6 | 5 | 10 | 10 | 9 | 6 | — | — | 9 |
| 599 | 10 | 4 | 7 | 7 | 10 | 10 | 10 | 7 | — | — | 10 |
| 600 | 2½ | 0 | — | 0 | — | — | 0 | 2 | — | — | 0 |
| 600 | 10 | 0 | 0 | — | 5 | 9 | 3 | 0 | — | — | 9 |
| 603 | 2½ | 2 | — | 2 | — | — | 7 | 6 | — | — | 5 |
| 603 | 5 | 1 | 2 | 3 | 10 | 9 | 6 | 6 | — | — | 7 |
| 605 | 5 | 0 | 0 | 2 | 8 | 10 | 6 | 3 | — | — | 7 |
| 605 | 10 | 0 | 4 | 3 | 10 | 10 | 10 | 7 | — | — | 9 |
| 608 | 5 | 3 | 7 | 5 | 10 | 10 | 10 | 8 | — | — | 10 |
| 608 | 10 | 4 | 8 | 7 | — | 10 | 9 | 9 | — | — | 9 |
| 610 | 5 | 3 | 0 | 4 | 10 | 10 | 5 | 4 | — | — | — |
| 610 | 10 | 2 | 6 | 5 | 5 | 8 | 6 | 5 | — | — | 5 |
| 612 | 5 | 0 | 0 | 1 | 2 | 3 | 6 | 4 | 0 | 8 | — |
| 612 | 10 | 0 | 0 | 0 | 3 | 4 | 6 | 4 | 1 | 8 | — |
| 613 | 5 | 0 | 0 | 0 | — | 7 | 3 | 0 | — | — | 5 |
| 613 | 10 | 0 | 0 | 0 | 4 | 3 | 1 | 3 | 2 | 4 | — |
| 617 | 5 | 1 | 0 | 2 | 4 | 10 | 2 | 3 | 3 | 10 | — |
| 617 | 10 | 1 | 3 | 3 | 5 | 10 | 3 | 5 | 10 | 10 | — |
| 625 | 5 | 0 | 0 | 1 | 2 | 0 | 0 | 0 | 0 | — | — |
| 625 | 10 | 0 | 0 | 1 | 2 | 6 | 2 | 2 | 2 | 8 | — |
| 633 | 5 | 0 | 0 | 0 | 2 | 2 | 0 | 0 | 0 | 0 | — |
| 633 | 10 | 2 | 0 | 2 | 3 | 4 | 0 | 0 | 0 | 0 | — |
| 634 | 5 | 2 | 5 | 5 | 6 | 10 | 10 | 8 | 5 | 3 | — |
| 634 | 10 | 3 | 6 | 6 | 8 | 10 | 10 | 8 | 3 | 9 | — |
| 640 | 5 | 3 | 5 | 4 | 5 | 10 | 10 | 6 | 3 | 8 | — |
| 640 | 10 | 4 | 10 | 6 | 8 | 10 | 10 | 8 | 7 | 10 | — |
| 647 | 5 | 0 | 0 | 0 | 5 | 10 | 0 | 0 | 3 | 0 | — |
| 647 | 10 | 3 | 2 | 1 | 8 | 10 | 0 | 6 | 7 | 5 | — |
| 648 | 5 | 3 | 7 | 4 | 5 | 6 | 10 | 6 | 5 | 8 | — |
| 648 | 10 | 5 | 9 | 5 | 7 | 8 | 10 | 8 | 5 | 10 | — |
| 650 | 5 | 0 | 2 | 2 | 3 | 6 | 3 | 2 | 4 | 2 | — |
| 650 | 10 | 1 | 3 | 2 | 5 | 3 | 3 | 4 | 5 | 8 | — |
| [2]Atrazine | 2½ | 0 | — | 0 | — | — | 10 | 10 | — | — | 10 |
| [2]Atrazine | 5 | 0 | 10 | 0 | — | 10 | 10 | 9 | — | — | 10 |
| Atrazine | 5 | 0 | 2 | 0 | 7 | 8 | 10 | 7 | 5 | 9 | — |
| Control | — | 0 | 0 | 0 | 0 | 0 | 0 | 0 | 0 | 0 | 0 |

[1]50-50 mixtures of compounds 585 and 586.
[2]Formulated as 80% wettable powder (with surfactants)

Certain of the data given in Table II above in connection with individual compounds was arithmetically averaged in order to give phytotoxicity ratings with respect to the compounds. In particular, the data generated during the five pound per acre dosage rate tests was used in order to give an average overall phytotoxicity rating, and ratings with respect to the weeds only, crops only, and corn and milo only. Again, the rating As can be seen from a study of the foregoing Tables II and III, the compounds of the present invention give excellent post-emergent herbicidal control of undesirable weeds. Furthermore, the phytotoxicity ratings given in Table III conclusively demonstrate that certain of the compounds of the invention have a high degree of selectivity for killing undesirable weeds while doing little or no damage to desirable crops such as especially corn and milo.

Having thus described the invention what is claimed as new and desired to be secured by Letters Patent is:

1. A method of inhibiting or stopping the growth of emergent weeds which comprise the steps of applying to the weed habitat from about ½ to 10 pounds per acre of a compound selected from the group consisting of (A) compounds of the formula

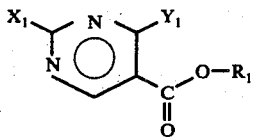

wherein $X_1$ represents chlorine or bromine, $Y_1$ is selected from the group consisting of the chlorine, bromine, alkylamino groups having from 1 to 6 carbon atoms, inclusive, hydroxyalkylamino groups having from 2 to 6 carbon atoms, inclusive, and alkoxy groups having from 1 to 6 carbon atoms, inclusive, and $R_1$ is selected from the group consisting of alkyl groups having from 1 to 18 carbon atoms, inclusive, benzyl groups, chlorophenyl groups, chlorobenzyl groups, trichloromethylalkyl groups having from 1 to 6 carbon atoms, inclusive, alkylphenyl, the alkyl groups having from 1 to 6 carbon atoms, inclusive, and alkenyl groups having from 3 to 6 carbon atoms, inclusive, and (B) compounds of the formula

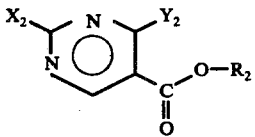

wherein $X_2$ is selected from the group consisting of alkoxy groups having from 1 to 6 carbon atoms, inclusive, alkylthio groups having from 1 to 6 carbon atoms, inclusive, and mercapto groups, $Y_2$ represents chlorine or bromine, and $R_2$ is selected from the group consisting of alkyl groups having from 1 to 18 carbon atoms, inclusive, benzyl groups, chlorophenyl groups, chlorobenzyl groups, trichloromethylalkyl groups having from 1 to 6 carbon atoms, inclusive, alkylphenyl, the alkyl groups having from 1 to 6 carbon atoms, inclusive, and alkenyl groups having from 3 to 6 carbon atoms, inclusive.

2. The method as set forth in claim 1 wherein said compound is selected from the group consisting of octyl 2,4-dichloropyrimidine-5-carboxylate, benzyl 2,4-dichloropyrimidine-5-carboxylate, ethyl 4-chloro-2-mercaptopyrimidine-5-carboxylate, butyl 2-chloro-4-di-n-propylaminopyrimidine-5-carboxylate, and allyl 2,4-dichloropyrimidine-5-carboxylate.

3. The method as set forth in claim 1 wherein said application is effected by dispersing said compound in a solvent therefor and spraying the resulting dispersion over the area where said plants are growing.

4. The method as set forth in claim 1 wherein $X_1$, $Y_1$, $X_2$ and $Y_2$ are chlorine.

5. The method as set forth in claim 1 wherein said compound is octyl 2,4-dichloropyrimidine-5-carboxylate.

6. The method as set forth in claim 1 wherein said compound is benzyl 2,4-dichloropyrimidine-5-carboxylate.

7. The method as set forth in claim 1 wherein said compound is ethyl 4-chloro-2-mercaptopyrimidine-5-carboxylate.

8. The method as set forth in claim 1 wherein said compound is butyl 2-chloro-4-di-n-propylaminopyrimidine-5-carboxylate.

9. The method as set forth in claim 1 wherein said compound is allyl 2,4-dichloropyrimidine-5-carboxylate.

* * * * *